US008323652B2

(12) United States Patent
Ni et al.

(10) Patent No.: US 8,323,652 B2
(45) Date of Patent: Dec. 4, 2012

(54) ANTIBODIES AGAINST GPIBα

(75) Inventors: Heyu Ni, North York (CA); Guangheng Zhu, Mississauga (CA)

(73) Assignee: Canadian Blood Services, Ottawa (CA)

( * ) Notice: Subject to any disclaimer, the term of this patent is extended or adjusted under 35 U.S.C. 154(b) by 58 days.

(21) Appl. No.: 12/618,224

(22) Filed: Nov. 13, 2009

(65) Prior Publication Data

US 2010/0150837 A1 Jun. 17, 2010

Related U.S. Application Data

(60) Provisional application No. 61/114,495, filed on Nov. 14, 2008.

(51) Int. Cl.
*A61K 39/395* (2006.01)
(52) U.S. Cl. ............... 424/143.1; 424/133.1; 424/141.1; 424/153.1; 514/13.5; 514/13.8; 514/14.9; 435/343; 530/387.3; 530/388.1; 530/388.22; 530/388.7
(58) Field of Classification Search .................. None
See application file for complete search history.

(56) References Cited

U.S. PATENT DOCUMENTS

| | | | | |
|---|---|---|---|---|
| 5,486,361 | A | * | 1/1996 | Gralnick ................ 424/144.1 |
| 5,530,101 | A | * | 6/1996 | Queen et al. ............ 530/387.3 |
| 5,770,198 | A | * | 6/1998 | Coller et al. ............ 424/153.1 |
| 5,777,085 | A | * | 7/1998 | Co et al. ................ 530/388.23 |
| 7,112,661 | B1 | * | 9/2006 | Miller .................... 530/387.1 |

FOREIGN PATENT DOCUMENTS

| | | |
|---|---|---|
| EP | 0990663 | 5/2000 |
| WO | 96/17622 | 6/1996 |
| WO | 00/26667 | 5/2000 |
| WO | 01/10911 | 2/2001 |
| WO | 2005/021711 | 3/2005 |

OTHER PUBLICATIONS

Janeway et al., Immunobiology, 3rd edition, Garland Publishing, pp. 3:1-3:11, 1997.
Kato et al., FEBS Lett. Aug. 9, 1993;328(1-2):49-54.
Ward et al., *Leucocyte Typing V: White Cell Differentiation Antigens Two Volume Set*: Epitope and functional characterization of the CD42 (gpIb/IX) mAb panel, Oxford University Press, USA, 1995, 1336-1337.
Zhu et al., "Novel mouse anti-mouse GPIbalpha monoclonal antibodies: development and characterization of new reagents for research in thrombosis and hemostasis," Journal of Thrombosis and Haemostasis; vol. 5, Supplement 2: PP-WE-060, 2007.
Bergmeier et al., "The role of platelet adhesion receptor GPIbα far exceeds that of its main ligand, von Willebrand factor, in arterial thrombosis," *Proc. Natl. Acad. Sci. USA* 103(45):16900-16905, 2006.
GenBank Accession No. NP_000164.1, Dec. 20, 2003, 6 pages.
GenBank Accession No. NP_034456.1, Sep. 25, 2007, 2 pages.
Ni et al., "Persistence of platelet thrombus formation in arterioles of mice lacking both von Willebrand factor and fibrinogen," *The Journal of Clinical Investigation* 106(3):385-392, 2000.
Ni et al., "Control of thrombus embolization and fibronectin internalization by integrin αIIbβ3 engagement of the fibrinogen γ chain," *Blood* 102(10):3609-3614, 2003.
Ni et al., "Plasma fibronectin promotes thrombus growth and stability in injured arterioles," *Proc. Natl. Acad. Sci. USA* 100(5):2415-2419, 2003.
Ni et al., "Platelets in hemostasis and thrombosis: role of integrins and their ligands," *Transfusion and Apheresis Science* 28:257-264, 2003.
Reheman et al., "Vitronectin stabilizes thrombi and vessel occlusion but plays a dual role in platelet aggregation," *Journal of Thrombosis and Haemostasis* 3:875-883, 2005.
Raheman et al., "Plasma fibronectin depletion enhances platelet aggregation and thrombus formation in mice lacking fibrinogen and von Willebrand factor," *Blood* 113(8):1809-1817, 2009.
Webster et al., "Relative efficacy of intravenous immunoglobulin G in ameliorating thrombocytopenia induced by antiplatelet GPIIbIIIa versus GPIbα antibodies," *Blood* 108(3):943-946, 2006.
Yang et al., "Fibrinogen and von Willebrand factor-independent platelet aggregation in vitro and in vivo," *Journal of Thrombosis and Haemostasis* 4:2230-2237, 2006.

\* cited by examiner

*Primary Examiner* — Michael Szperka
(74) *Attorney, Agent, or Firm* — Seed IP Law Group PLLC

(57) ABSTRACT

This application relates to agents capable of specifically recognizing GPIbα, a key receptor required for platelet adhesion and aggregation. More specifically, this application relates to monoclonal antibodies and derivatives thereof capable of specifically recognizing both the murine and the human GPIbα. These monoclonal antibodies and derivatives are particularly useful in the treatment or prevention of thrombosis as well as research tools.

21 Claims, 14 Drawing Sheets

ANTIBODIES AGAINST GPIBα

CROSS-REFERENCE TO RELATED APPLICATIONS AND BIOLOGICAL DEPOSITS

This application claims priority from U.S. provisional patent application 61/114,495 filed on Nov. 14, 2008; which application is incorporated herein in its entirety.

This application refers to and comprises nine biological deposits (hybridomas) accepted at the International Depositary Authority of Canada on Oct. 7, 2008 under Accession Numbers 071008-01 (NIT A1 clone), 071008-02 (NIT B1 clone), 071008-03 (NIT C1 clone), 071008-04 (NIT D1 clone), 071008-05 (NIT E1 clone), 071008-06 (NIT F1 clone), 071008-07 (NIT G1 clone), 071008-08 (NIT H1 clone), 071008-09 (NIT I1 clone). The viability of these clones was tested on Oct. 15, 2008. These biological deposits have been made in accordance with the *Budapest Treaty*. The content of these biological deposits are incorporated herein by reference.

BACKGROUND

1. Technical Field

The present invention relates to monoclonal antibodies, and more specifically, to monoclonal antibodies that specifically recognize platelet GPIbα. These antibodies are useful, for instance, in antithrombotic therapy and in diagnostics, as well as in animal models of thrombosis, hemostasis, thrombocytopenia, and anti-angiogenesis.

2. Description of the Related Art

Platelet adhesion and aggregation are key events required to arrest bleeding. However, the same processes also contribute to the generation of thrombi within atherosclerotic arteries such as the coronary or cerebral arteries, which is the worldwide leading cause of morbidity and mortality.

Platelet GPIbα is an important platelet receptor which mediates platelet adhesion to the vessel wall by interacting with, for example, the von Willebrand factor (Wolfgang et al., 2006, PNAS, 103:16900-16905). Once a platelet is anchored to the vessel wall, it facilitates the aggregation of other platelets (Ni H et al. 2003 Transfus Apher Sci. 28: 257-64 and Wolfgang et al., 2006, PNAS, 103:16900-16905). Since GPIbα is involved in the early stages of thrombosis, antagonists of platelet GPIbα have a great potential for anti-thrombotic therapy and could prevent vessel occlusion. Currently, there is no therapy in the market that specifically targets GPIbα.

Antagonists targeting GPIbα would provide significant advantages as compared with other anti-platelet drugs such as those antagonists to β3 integrin (also known as GPIIbIIIa), such as ReoPro™ approved 1994, Integrinlin™ approved 1998, Aggrastat™ approved 1998, already in the market. The prevailing view is that antagonists of GPIbα may prevent the thrombus formation at an earlier stage than β3 integrin antagonists, and as such would be more potent and would exhibit less side effects than β3 antagonists (e.g., bleed tendency observed in antagonists to the GPIIbIIIa receptor).

Monoclonal antibodies against GPIbα are readily available and currently used in the art. However, these antibodies have been made in wild-type animals (e.g., mice) and, as such, do not recognize the mouse GPIbα. Since mouse and human GPIbα are similar polypeptides (e.g., they possess an important degree of homology), the use of a wild-type mouse to generate the monoclonal antibodies limits the repertoire of the antibodies produced to epitopes present on the human GPIbα and absent on the mouse GPIbα.

In light of the above, it would be highly desirable to be provided with antibodies or compositions derived therefrom capable of specifically recognizing the platelet GPIbα receptor. Those agents would preferably specifically recognize both the human and the mouse GPIbα receptors on platelets. Those agents are preferably antibodies, such as monoclonal antibodies, capable of specifically recognizing and/or neutralizing the platelet GPIbα receptor.

BRIEF SUMMARY

According to one aspect, the present invention relates to an hybridoma cell line having IDAC Accession No. 071008-01 (NIT A1 clone) filed on Oct. 7, 2008, an hybridoma cell line having IDAC Accession No. 071008-02 (NIT B1 clone) filed on Oct. 7, 2008, an hybridoma cell line having IDAC Accession No. 071008-03 (NIT C1 clone) filed on Oct. 7, 2008, an hybridoma cell line having IDAC Accession No. 071008-04 (NIT D1 clone) filed on Oct. 7, 2008, an hybridoma cell line having IDAC Accession No. 071008-05 (NIT E1 clone) filed on Oct. 7, 2008, an hybridoma cell line having IDAC Accession No. 071008-06 (NIT F1 clone) filed on Oct. 7, 2008, an hybridoma cell line having IDAC Accession No. 071008-07 (NIT G1 clone) filed on Oct. 7, 2008, an hybridoma cell line having IDAC Accession No. 071008-08 (NIT H1 clone) filed on Oct. 7, 2008 and/or an hybridoma cell line having IDAC Accession No. 071008-09 (NIT I1 clone) filed on Oct. 7, 2008.

According to a further aspect, the present invention also relates to an isolated and purified antibody produced by the hybridoma cell line described herein. In an embodiment, the isolated and purified antibody is humanized. In another embodiment, the isolated and purified antibody is labeled with a detectable marker or a conjugate. In another embodiment, the detectable marker is at least one of a gold marker, a fluorescent marker and radioactive marker. In a further embodiment, the conjugate is at least one of biotin, peroxidase, alkaline phosphatase, glucose oxidase and phycobiliprotein. According to yet a further embodiment, the isolated and purified antibody is recognized by a labeled antibody.

According to another aspect, the present invention relates to a fragment of an isolated and purified antibody produced by the hybridoma cell line described herein. In an embodiment, the fragment is humanized. In still another embodiment, the fragment is labeled with a detectable marker or a conjugate. In yet a further embodiment, the detectable marker is at least one of a gold marker, a fluorescent marker and a radioactive marker. In still another embodiment, the conjugate is at least one of biotin, peroxidase, alkaline phosphatase, glucose oxidase and phycobiliprotein. In yet a further embodiment, the fragment is recognized by a labeled antibody.

According to still another aspect, the present invention provides a pharmaceutical composition comprising the isolated and purified antibody of any described herein or the fragment described herein and a pharmaceutical acceptable carrier. In an embodiment, the pharmaceutical composition is for inhibiting platelet aggregation. In another embodiment, the pharmaceutical composition is for the treatment of thrombosis.

According to yet another aspect, the present invention provides a solid phase having attached thereto the isolated and purified antibody described herein or the fragment described herein. In an embodiment, the solid phase is for the separation or isolation of a GPIbα receptor. In another embodiment, the solid phase is for the separation or isolation of a platelet. In still another embodiment, the solid phase comprises at least one of a gel, a hydrogel, a resin, a bead, nitrocellulose, a nylon membrane, a micrometer plate, a culture flask, a polymeric material and glass.

According to another aspect, the present invention provides a method for preventing the formation of a thrombus and/or the aggregation of platelets in an individual, said method comprising administering the isolated and purified antibody described herein or the fragment described herein in the individual, thereby preventing the formation of the thrombus and/or the aggregation of platelets. In an embodiment, the administration of the isolated and purified antibody or the fragment limits the size of the thrombus and/or the aggregation of platelets. In still another embodiment, the administration of the isolated and purified antibody or the fragment limits the number of thrombi in the individual. In yet another embodiment, the individual is also administered with a further antithrombotic agent.

According to still another aspect, the present invention provides use of the isolated and purified antibody described herein or the fragment described herein for the prevention of the formation of a thrombus and/or the aggregation of platelets in an individual.

According to still yet another aspect, the present invention provides a method of resolving thrombosis in an individual having a thrombus, said method comprising administering the isolated and purified antibody described herein or the fragment described herein in the individual, thereby resolving thrombosis in the individual. In an embodiment, the administration of the isolated and purified antibody or the fragment limits the size of the thrombus. In another embodiment, the isolated and purified antibody or the fragment limits the number of thrombi. In yet another embodiment, the individual is also administered with a further antithrombotic agent.

According to another aspect, the present invention provides use of the isolated and purified antibody described herein or the fragment described herein for the resolution of thrombosis in an individual having a thrombus.

According to another aspect, the present invention also provides a method for determining the presence of a thrombus in an individual, said method comprising administering the isolated and purified antibody described herein or the fragment described herein to the individual, allowing the isolated and purified antibody or the fragment to form a complex with a GPIbα receptor on a platelet and determining the presence of the complex. In an embodiment, the individual has received an antithrombotic agent prior to or after the administration of the isolated and purified antibody or the fragment. In another embodiment, the determination of the presence of the complex is repeated in time. In another embodiment, the individual is an animal. In a further embodiment, the animal is a rodent and, in a yet a further embodiment, the rodent is a mouse.

According to still another aspect, the present invention provides use of the isolated and purified antibody described herein or the fragment described herein for the determination of the presence of a thrombus in an individual.

According to another aspect, the present invention provides a method for determining platelet count in a sample from an individual, said method comprising contacting the isolated and purified antibody described herein or the fragment described herein with the sample from the individual to form a complex between (i) the isolated and purified antibody of the fragment and (ii) the platelet and detecting the presence of the complex to determine the platelet count in the sample.

According to another aspect, the present invention provides a method for tracking a platelet in an individual, said method comprising administering the isolated and purified antibody described herein or the fragment described herein to the individual, allowing for a complex between (i) the isolated and purified antibody or the fragment and (ii) the platelet to be formed, detecting the location of the complex to track the platelet. In an embodiment, the detection is repeated in time. In another embodiment, the individual is an animal. In a further embodiment, the animal is a rodent and, in a yet a further embodiment, the rodent is a mouse.

According to yet another aspect, the present invention provides use of the isolated and purified antibody described herein or the fragment described herein for the determination of the presence of a thrombus in an individual.

DETAILED DESCRIPTION

Figure 1:
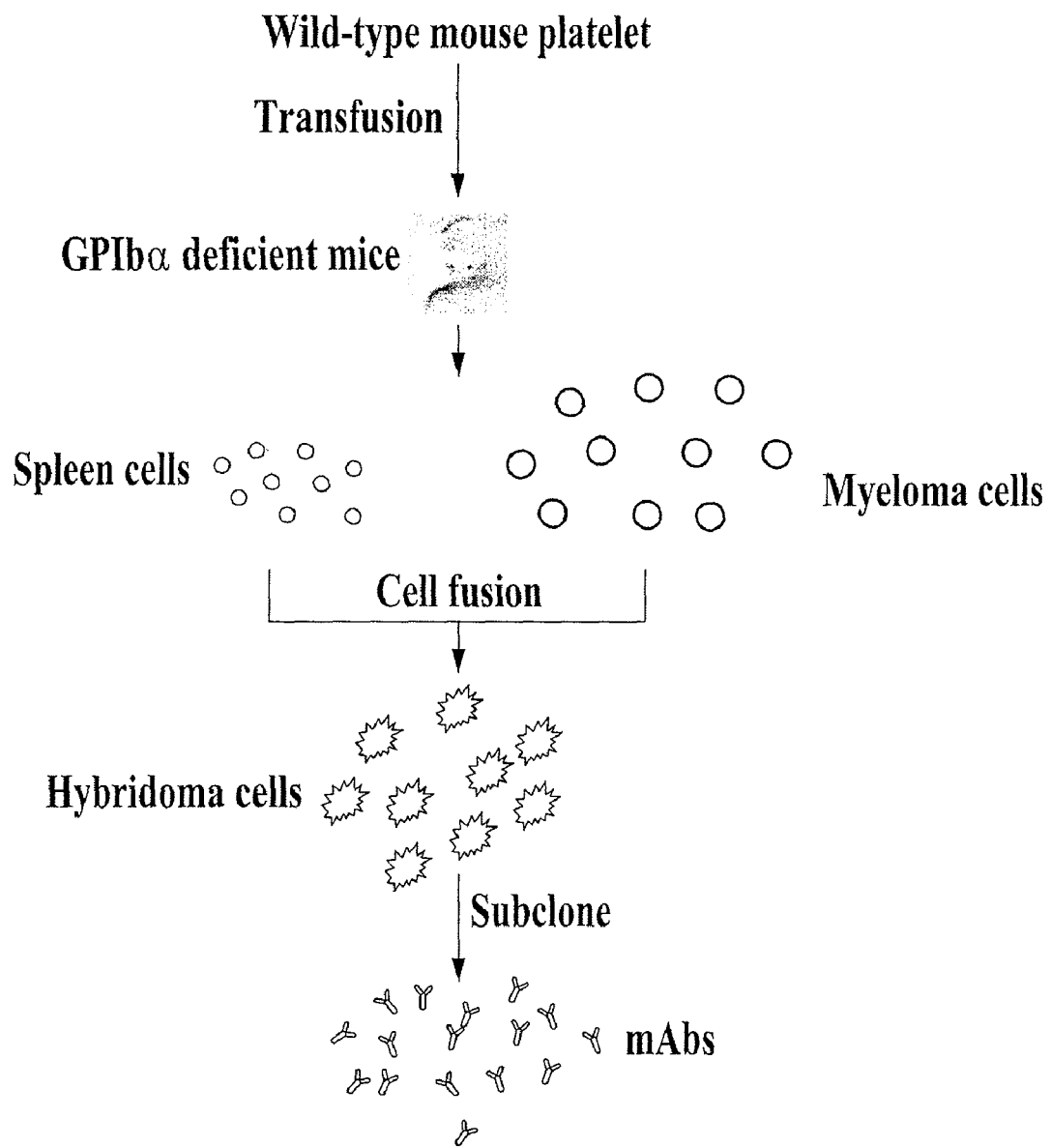
FIG. 1 illustrates a flow diagram illustrating a method for generating monoclonal antibodies (mAbs) using GPIbα gene knockout mice.

This application relates to agents capable of specifically recognizing GPIbα, a key receptor required for platelet adhesion and aggregation. As used herein, the terms "GPIbα" and "GPIbα" are used interchangeably and refer to the same receptor that is present on platelets. The GPIbα GenBank reference number for the human version is NP_000164 and for the mouse version is NP_034456. More specifically, this application relates to monoclonal antibodies (mAbs) and derivatives thereof capable of specifically recognizing both the murine and the human GPIbα. In an embodiment, these antibodies can also recognize the pig, rabbit, rat, goat, and sheep GPIbα. These monoclonal antibodies and derivatives are particularly useful in the treatment and/or prevention of thrombosis as well as research tools. These mAbs can also be useful in the diagnosis for several GPIbα-related diseases such as Bernard-Soulier syndrome and immune thrombocytopenia.

GPIbα interaction with VWF play a critical role for platelet adhesion and aggregation. Since GPIbα is involved in the early stages of thrombosis, antagonists of platelet GPIbα have great potential for anti-thrombotic therapy and prevent vessel occlusion, which would provide significant advantages as compared with other anti-platelet drugs such as those antagonists to β3 integrin. However, in the art, there is no GPIbα antagonist commercially available. Current monoclonal antibodies (mAbs) against human GPIbα have been made in wild-type mice. However, since mouse and human GPIbα are very similar polypeptides and since the immune system usually does not respond to self antigens (such as GPIbα), this approach limits the repertoire of the antibodies produced to epitopes presented on the human GPIbα and absent on the mouse GPIbα. Monoclonal antibodies produced using conventional techniques therefore cannot recognize mouse GPIbα. Using GPIbα-gene deficient mice immunized with wild-type platelets, Applicant firstly generated anti-GPIbα mAbs which recognize not only mouse but also human GPIbα. The mAbs produced inhibit platelet adhesion and thrombus growth. Compare with current available antibodies, these monoclonal antibodies are believed to recognize different epitopes of GPIbα on platelets. These antibodies can be potential anti-thrombotic drugs and useful reagents for hemostasis and thrombosis research.

Traditional methods to generate monoclonal antibodies (mAbs) against human proteins usually use wild-type BALB/c mice. The antigenicity of a human protein, and thus the ability to generate mAbs using such methods, will be based on the difference between the human and murine protein sequences. Since GPIbα is relatively highly conserved between these two species (~50-60% identity), the repertoire of antibodies against human GPIbα integrin in wild-type BALB/c mice is limited. In the art, the mAbs generated by the traditional method do not recognize both murine and human GPIbα.

In order to circumvent this limitation, Applicant has generated novel mAbs by using GPIbα-deficient BALB/c mice, which do not express GPIbα and can thus produce antibodies against any portion of GPIbα. The repertoire of antibodies against GPIbα using this methodology is much larger compared to using wild-type mice since antibodies can be generated against the entire GPIbα protein, even in the regions highly conserved between the murine and the human version. The GPIbα knocked-out mice have then been transfused with wild-type platelet (e.g., wild-type mouse platelets). Hybridomas have been generated with the spleens of these mice. Using this technology, nine monoclonal antibodies (mAbs) (NIT-A, B, C, D, E, F, G, H and I) were obtained from GPIbα deficient mice after wild-type mouse platelet transfusions. These antibodies specifically bind to mouse GPIbα. Three clones (NIT-A, B and F) also bind human and rat platelets. Two clones (NIT-C and D) also bind pig platelets. As it will be shown herein, some clones can completely inhibit human platelet aggregation induced by ristocetin, and therefore may have potential for antithrombotic therapy (e.g., inhibitory mAbs). The other antibodies produced do not affect platelet adhesion and aggregation (neutral mAbs). The mAbs produced (including both inhibitory and neutral mAbs) have potential to be used as diagnostic reagents (e.g., Bernard-Soulier syndrome and immune thrombocytopenia). The radioactive isotope labeled neutral mAbs can be used to track platelet circulation in vivo. These mAbs are important research tools for thrombosis and hemostasis including animal models of these human diseases.

Accordingly, the present application relates to the hybridoma cell lines that have been produced according to the method described herein. Some of these hybridoma cell lines have been deposited in the International Depositary Authority of Canada on Oct. 7, 2008 under Accession Numbers 071008-01 (NIT A1 clone), 071008-02 (NIT B1 clone), 071008-03 (NIT C1 clone), 071008-04 (NIT D1 clone), 071008-05 (NIT E1 clone), 071008-06 (NIT F1 clone), 071008-07 (NIT G1 clone), 071008-08 (NIT H1 clone), and 071008-09 (NIT I1 clone).

The present application also relates to the antibodies produced by the hybridoma cell lines described herewith as well as derivatives and fragments of those antibodies. Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by Kabat et al. (Kabat, E. A. et al., Sequences of Proteins of Immunological Interest, Fifth Edition, U.S. Department of Health and Human Services, U.S. Government Printing Office (1991)).

Antibody derivatives include, but are not limited to, humanized antibodies. As used herein, the term "humanized antibody" refers to an immunoglobulin that comprises both a region derived from a human antibody or immunoglobulin and a region derived from a non-human antibody or immunoglobulin. The action of humanizing an antibody consists in substituting a portion of a non-human antibody with a corresponding portion of a human antibody. For example, a humanized antibody as used herein could comprise a non-human region variable region (such as a region derived from a murine antibody) capable of specifically recognizing GPIbα and a human constant region derived from a human antibody. In another example, the humanized immunoglobulin can comprise a heavy chain and a light chain, wherein the light chain comprises a complementarity determining region derived from an antibody of non-human origin which binds GPIbα and a framework region derived from a light chain of human origin, and the heavy chain comprises a complementarity determining region derived from an antibody of non-human origin which binds GPIbα and a framework region derived from a heavy chain of human origin.

As used herein, the present application also relates to fragments of the monoclonal antibodies described herein. As used herein, a "fragment" of an antibody (e.g., a monoclonal antibody) is a portion of an antibody that is capable of specifically recognizing the same epitope as the full version of the antibody. In the present patent application, antibody fragments are capable of specifically recognizing GPIbα. Antibody fragments include, but are not limited to, the antibody light chain, single chain antibodies, Fv, Fab, Fab' and F(ab')$_2$ fragments. Such fragments can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a chimeric gene encoding the heavy chain of an F(ab')$_2$ fragment can be designed to include DNA sequences encoding the CH$^1$ domain and hinge region of the heavy chain. Antibody fragments can also be humanized. For example, a humanized light chain comprising a light chain CDR (i.e., one or more CDRs) of non-human origin and a human light chain framework region. In another example, a humanized immunoglobulin heavy chain can comprise a heavy chain CDR (i.e., one or more CDRs) of non-human origin and a human heavy chain framework region. The CDRs can be derived from a non-human immunoglobulin.

In research, the capacity of antibodies to specifically recognize an epitope on a specific polypeptide is used to detect (e.g., visualize) the polypeptide. The antibodies described herein can be used for the detection of GPIbα in immunohistology, immunofluorescence, immunoblot, electron microscopy, and/or immunoprecipitation. In order to do so, the antibodies must first be labeled or adapted to be used with a second (or third) antibody that is labeled. In an embodiment, the antibodies and fragments presented herein can be labeled with a detectable marker or a conjugate. This is particularly advantageous when the antibodies are to be used as diagnostic or research tools. The detectable markers include, but are not limited to gold (for electron microscopy applications), a fluorescent marker (for immunofluorescence and flow cytometry applications) and a radioactive marker (for diagnostic purposes). For example, if the antibodies, derivatives or fragments are labeled to a radioisotope, they could also be used in in vivo diagnostic methods. Conjugates used as labels are particularly useful in assays involving enzymes (such as ELISA). Useful conjugates are numerous and include biotin, peroxidase, alkaline phosphatase, glucose oxidase and phycobiliprotein, and radioisotope. The antibodies and fragments thereof could also be detected indirectly by coupling a label to another antibody that specifically recognized the anti-GPIbα antibodies or the fragments thereof. In this particular embodiment, the use of a further antibody can increase the signal obtained.

As antibodies (as well as derivatives or fragments thereof) are extensively used in the research setting for purifying or isolating polypeptides, the antibodies described herein (as well as derivatives or fragments thereof) could also be successfully used for the purification (e.g., immunopurification or immunoprecipitation) or the isolation of the GPIbα (human or mouse) polypeptide and/or the platelet expressing the GPIbα. Antibodies are also used in assay for detecting the presence of a particular polypeptide in a sample, such as a ELISA, a sandwich ELISA or a polypeptide microarray. As such, the antibodies described herein could also be used for the detection of GPIbα (human and/or mouse) in a sample. For both of these applications (purification and/or detection), the antibodies are usually linked to a solid carrier. Accordingly, in one additional embodiment, the present application provides a solid phase having attached thereto the antibodies described herein (as well as derivatives thereof and fragments thereof). The solid phase can be, but is not limited to a gel, a hydrogel, a resin, a bead, nitrocellulose, nylon membrane, a micrometer or microtiter plate, a culture flask, a polymeric material and/or glass.

In a further embodiment, the present application also contemplates the use of the antibodies of fragments thereof described herein in pharmaceutical compositions. The pharmaceutical compositions optionally also comprise a pharmaceutical acceptable carrier. As used herein a "carrier" or "pharmaceutical carrier" is a pharmaceutically acceptable solvent, suspending agent or any other pharmacologically inert vehicle for delivering one or more antibody or fragment thereof to an individual. Because antibodies or fragments thereof are large compounds, there are preferably injected in the individual. A pharmaceutical carrier is generally selected to provide for the desired bulk, consistency, etc., when combined with components of a given pharmaceutical composition, in view of the intended administration mode. Typical pharmaceutical carriers include, but are not limited to binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.);

disintegrants (e.g., starch, sodium starch glycotate, etc.); and wetting agents (e.g., sodium lauryl sulphate, etc.).

In yet a further embodiment, the present application also contemplates the use of the antibodies or fragments thereof described herein in diagnostic compositions. The diagnostic compositions optionally also comprise an acceptable carrier that is suited for the diagnostic use of the antibodies.

Antibodies or fragments thereof disclosed in the present application may be administered with a pharmaceutically-acceptable carrier in unit dosage form. Conventional pharmaceutical practice may be employed to provide suitable formulations or compositions to administer such compositions to individuals. Although injection is preferred, any appropriate route of administration may be employed, for example, oral, intravenous, parenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. Therapeutic formulations may be in the form of liquid solutions or suspension; for oral administration, formulations may be in the form of tablets or capsules; and for intranasal formulations, in the form of powders, nasal drops, or aerosols.

Methods well known in the art for making formulations are found in, for example, *Remington: The Science and Practice of Pharmacy*, (19th ed.) ed. A. R. Gennaro AR., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

In addition, the term "pharmaceutically effective amount" or "therapeutically effective amount" refers to an amount (dose) effective in treating an individual. It is also to be understood herein that a "pharmaceutically effective amount" may be interpreted as an amount giving a desired therapeutic effect, either taken in one dose or in any dosage or route, taken alone or in combination with other therapeutic agents.

A therapeutically effective amount or dosage of an antibody or fragment thereof disclosed herein or a pharmaceutical composition comprising the antibody or fragment thereof, may range from about 0.001 to 30 mg/kg body weight, with other ranges including about 0.01 to 25 mg/kg body weight, about 0.025 to 10 mg/kg body weight, about 0.3 to 20 mg/kg body weight, about 0.1 to 20 mg/kg body weight, about 1 to 10 mg/kg body weight, 2 to 9 mg/kg body weight, 3 to 8 mg/kg body weight, 4 to 7 mg/kg body weight, 5 to 6 mg/kg body weight, and 20 to 50 mg/kg body weight. In other embodiments, a therapeutically effective amount or dosage may range from about 0.001 to 50 mg total, with other ranges of the invention including about 0.01 to 10 mg, about 0.3 to 3 mg, about 3 to 10 mg, about 6 mg, about 9 mg, about 10 to 20 mg, about 20-30 mg, about 30 to 40 mg, and about 40 to 50 mg.

Because of the intrinsic properties of the antibodies disclosed herein, the pharmaceutical compositions are particularly useful for the inhibition of platelet adhesion and aggregation (such as a thrombus or a blood clot) in an individual and/or the treatment or prevention of thrombosis in an individual.

According to an embodiment, there is provided a method for the prevention of the formation of a blood clot in an individual. In this particular embodiment, only the antibodies that are capable of limiting the interaction of GPIbα (human or mouse) with its cognate ligand (such as the von Willebrand factor) can be successfully used. The method comprises the administration of the antibody described herein as well as derivatives thereof and/or fragments thereof or the administration a pharmaceutical composition as described herein. In a further embodiment, the administration of the antibody or the pharmaceutical composition does not completely prevent the formation of the blood clot or thrombus but limits its size. In a further embodiment, the administration of the antibody or the pharmaceutical composition does not completely prevent the formation of all the blood clots or thrombi in an individual by limits their number. In yet a further embodiment, the individual could also be administered with another antithrombotic agent, such as those commonly used in the art (for example heparin or an antagonist of a β3 integrin such as ReoPro™). Use of the antibodies described herein or the pharmaceutical compositions described herein for the prevention of the formation of a blood clot or thrombus is also contemplated.

According to an embodiment, there is provided a method for the resolution of thrombosis in an individual having at least one blood clot. As used herein, the term "resolution" refers to the subsidence of thrombosis. In this particular embodiment, preferably the antibodies that are capable of limiting the interaction of GPIbα (human or mouse) with its cognate ligand (such as the von Willebrand factor) can be successfully used. The method comprises the administration of the antibody described herein as well as derivatives thereof and/or fragments thereof or the administration a pharmaceutical composition as described herein. In a further embodiment, the administration of the antibody or the pharmaceutical composition does not completely eliminate the blood clot or thrombus by limits its size. In a further embodiment, the administration of the antibody or the pharmaceutical composition does not completely eliminate all the blood clots or thrombi in an individual by limits their number. In yet a further embodiment, the individual could also be administered with another antithrombotic agent, such as those commonly used in the art. Use of the antibodies described herein or the pharmaceutical compositions described herein for the resolution of thrombosis in an individual is also contemplated.

According to an embodiment, there is provided a method for determining the presence of a platelet rich thrombi (blood clot) in an individual. Platelet rich thrombi or white thrombi are the major cause of vessel occlusion in arteries and are the most common mechanism leading to myocardial or cerebral infarction (i.e., heart attack and stroke). In this particular embodiment, antibodies that are capable of recognizing platelet specific proteins (e.g., GPIbα (human or mouse) which is abundant on platelet surface) can be successfully used. The method comprises the administration of the antibody described herein as well as derivatives thereof and/or fragments thereof. The method also comprises allowing the antibody to form a complex. The method further comprises detecting the complex. The complex can be directly detected by labeling the antibody with an appropriate marker. The complex can also be detected indirectly by, for example, the administration of a second (or third) labeled antibody capable of recognizing the first antibody. The determination of the presence of the complex can be done once, or it can be repeated in time to determine the evolution or regression of the clot or thrombus. In an embodiment, the individual has developed a platelet rich thrombus (blood clot) prior to the administration of the antibody. In yet a further embodiment, the individual could also be administered with an antithrombotic agent, such as those commonly used in the art. In this particular embodiment, the detection, especially if it is repeated in time (e.g., prior to and after the administration of the antithrombotic agent), will generate valuable information about the efficiency of the antithrombotic drug to resolve the thrombosis. In an embodiment, the individual is an animal. In a further embodiment, the animal is a rodent, such as a mouse or a rat. Use of the antibodies described herein for the detection of a clot or thrombus in an individual is also contemplated.

According to an embodiment, there is provided a method for determining platelet count in sample from an individual. In this particular embodiment, antibodies that are capable of specifically recognizing GPIbα (human or mouse) can be successfully used. The method comprises contacting the antibody described herein as well as derivatives thereof and/or fragments thereof with the sample. The method also comprises allowing a complex between the antibody and the platelet to be formed and detecting such complex. The complex can be directly detected by labeling the antibody with an appropriate marker. The complex can also be detected indirectly by, for example, the administration of a second (or third) labeled antibody capable of recognizing the first antibody.

According to an embodiment, there is provided a method for tracking a platelet in an individual. In this particular embodiment, antibodies that are capable of specifically recognizing GPIbα (human or mouse) can be successfully used. The method comprises administering the antibody described herein as well as derivatives thereof and/or fragments thereof with the sample. The method also comprises allowing a complex between the antibody and the platelet to be formed and detecting such complex. The complex can be directly detected by labeling the antibody with an appropriate marker. The complex can also be detected indirectly by, for example, the administration of a second (or third) labeled antibody capable of recognizing the first antibody. The tracking of the platelet can be done once, or it can be repeated in time to determine the behavior of the platelet. In an embodiment, the individual has developed a blood clot prior to the administration of the antibody. In yet a further embodiment, the individual could also be administered with an antithrombotic agent, such as those commonly used in the art. In this particular embodiment, the detection, especially if it is repeated in time (e.g., prior to and after the administration of the antithrombotic agent), will generate valuable information about the effects of the antithrombotic drug to on the behavior of platelets. In an embodiment, the individual is an animal. In a further embodiment, the animal is a rodent, such as a mouse or a rat. Use of the antibodies described herein for the tracking of a platelet in an individual is also contemplated.

The present invention will be more readily understood by referring to the following examples which are given to illustrate the invention rather than to limit its scope.

EXAMPLE I

Production of the Monoclonal Antibodies Against GPIbα

Monoclonal antibodies were produced in accordance with the scheme illustrated in FIG. 1. Briefly, BALB/C wild type mice were bled under ether anesthesia from retro-orbital plexus using heparin-coated glass capillary tubes. The blood was collected into a tube containing 3% ACD (1/9, v/v). Platelet rich plasma was obtained by centrifugation at 300 g for 7 minutes. Platelets were then isolated from the platelet rich plasma using a Sepharose 2B column in PIPES buffer (PIPES 5 mM, NaCl 1.37 mM, KCl 4 mM, Glucose 0.1%, pH 7.0) as previously described (Ni, H. et al. 2000. J Clin Invest 106: 385-392; Yang, H. et al. 2006 J Thromb Haemost 4: 2230-2237; Reheman A. et al. Blood. 2009; February 19. 113: 1809-1817). GPIbα-deficient BALB/C mice, 6 to 8 weeks of age, were transfused with $1 \times 10^8$ these gel-filtered BALB/c wild-type mouse platelets for 6 times, once a week. Transfused GPIbαdeficient BALB/C mice spleen cells were fused with mouse myeloma cells (Ag 8.653), and hybridomas were selected in HAT medium. Hybridomas secreting mAbs directed against GPIbαwere identified by flow cytometry, and subcloned twice before large-scale production.

Monoclonal antibodies were produced and purified according to standard methods. Briefly, antibody positive hybridoma cells were transferred into commercial HyQ ADCF-MAb sera-free medium (HyClone, Logan, Utah, USA) in cell culture flasks (500 ml). Hybridoma cells were allowed to grow until they die, then the medium was collected. The medium was centrifuged at 5000 rpm, for 20 minutes at room temperature to remove the cells. The supernatant was collected, and diluted 1:1 with commercial ImmunoPure™ IgG Binding Buffer (Pierce Biotechnology, Inc. Rockford, Ill., USA), then passed through a Protein G coupled sepharose column. Subsequently, the column was washed with binding buffer, and antibody was eluted after adding commercial ImmunoPure™ IgG Elution Buffer (Pierce Biotechnology, Inc.). The fractions of antibodies in elution buffer were collected in individual Eppendorf™ tubes. The optical density (OD) of each fraction was measured at A280 (to detect proteins), and the high concentration fractions were dialysed using a dialysis membrane in phosphate buffered saline.

EXAMPLE II

Subtypes Characterization of the Monoclonal Antibodies Specific for GPIbα

Washed mouse platelets ($1 \times 10^6$) were incubated one hour with PBS (control), or a mAb produced according to the protocol set forth in Example I. The platelets were then stained with FITC-labeled goat anti-mouse IgG, $IgG_1$, $IgG_{2a}$, $IgG_{2b}$ or $IgG_3$ (Sigma) for 45 min. Samples were analyzed by flow cytometry (FACScan™ Becton Dickinson).

Figure 2A:
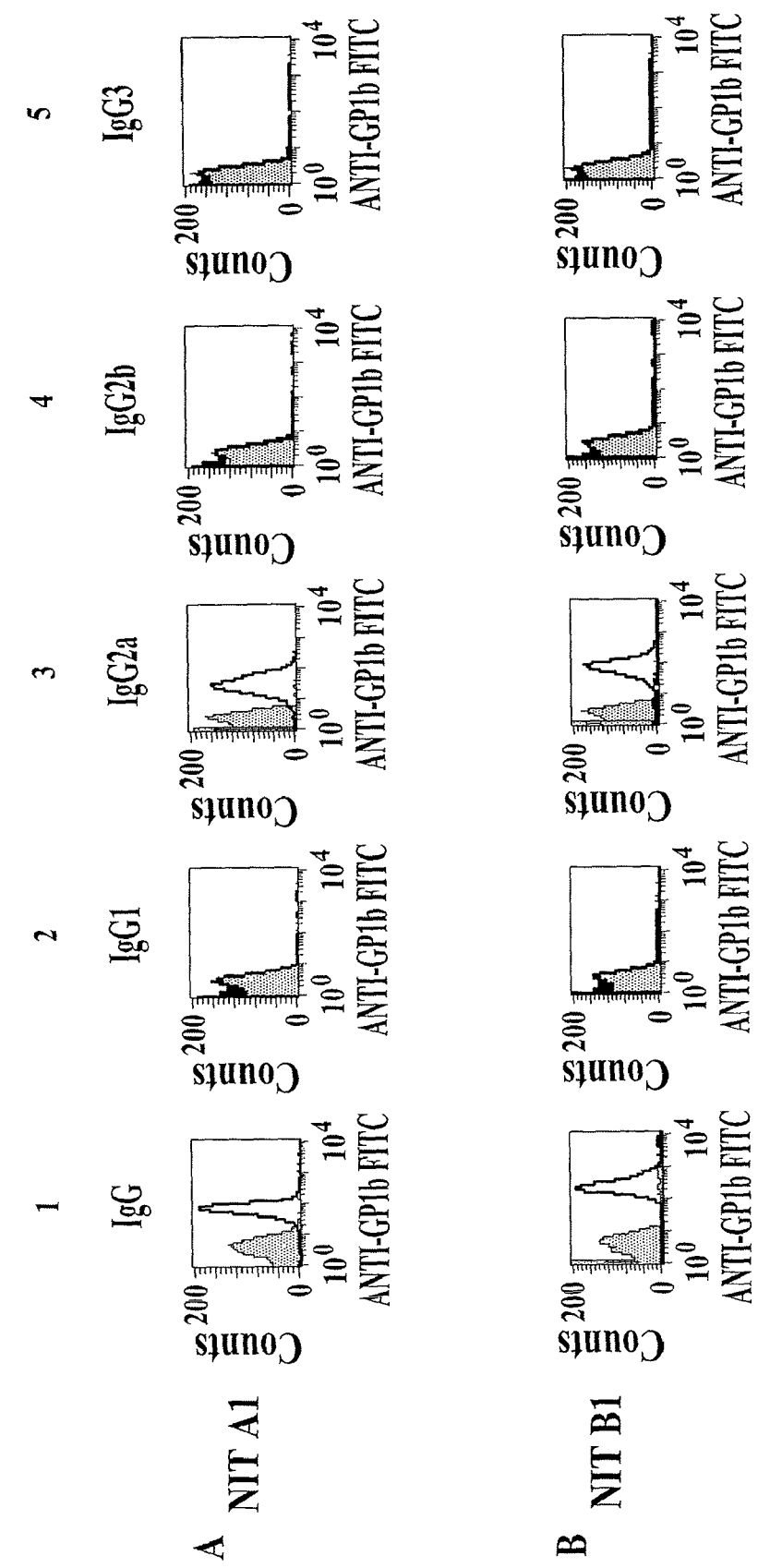
FIGS. 2A and B are graphical representations of flow cytometry results (counts in functions of fluorescence) for the identification of the type and subtype of immunoglobulins of the various clones. On FIG. 2A, line A represents clone NIT A1, line B clone NIT B1, line C clone NIT C1 and line D, NIT D1. On FIG. 2B, line A represents clone NIT E1, line B clone NIT F1. line C clone NIT G1, line D clone NIT H1 and line E NIT I1. On both FIGS. 2A and 2B, column 1 represents results obtained with an anti-IgG antibody, column 2 represents results obtained with an anti-IgG$_1$ antibody, column 3 represents results obtained with an anti-IgG$_{2a}$ antibody, column 4 represents results obtained with an anti-IgG$_{2b}$ antibody and column 5 represents results obtained with an anti-IgG$_3$ antibody.
Figure 2A:
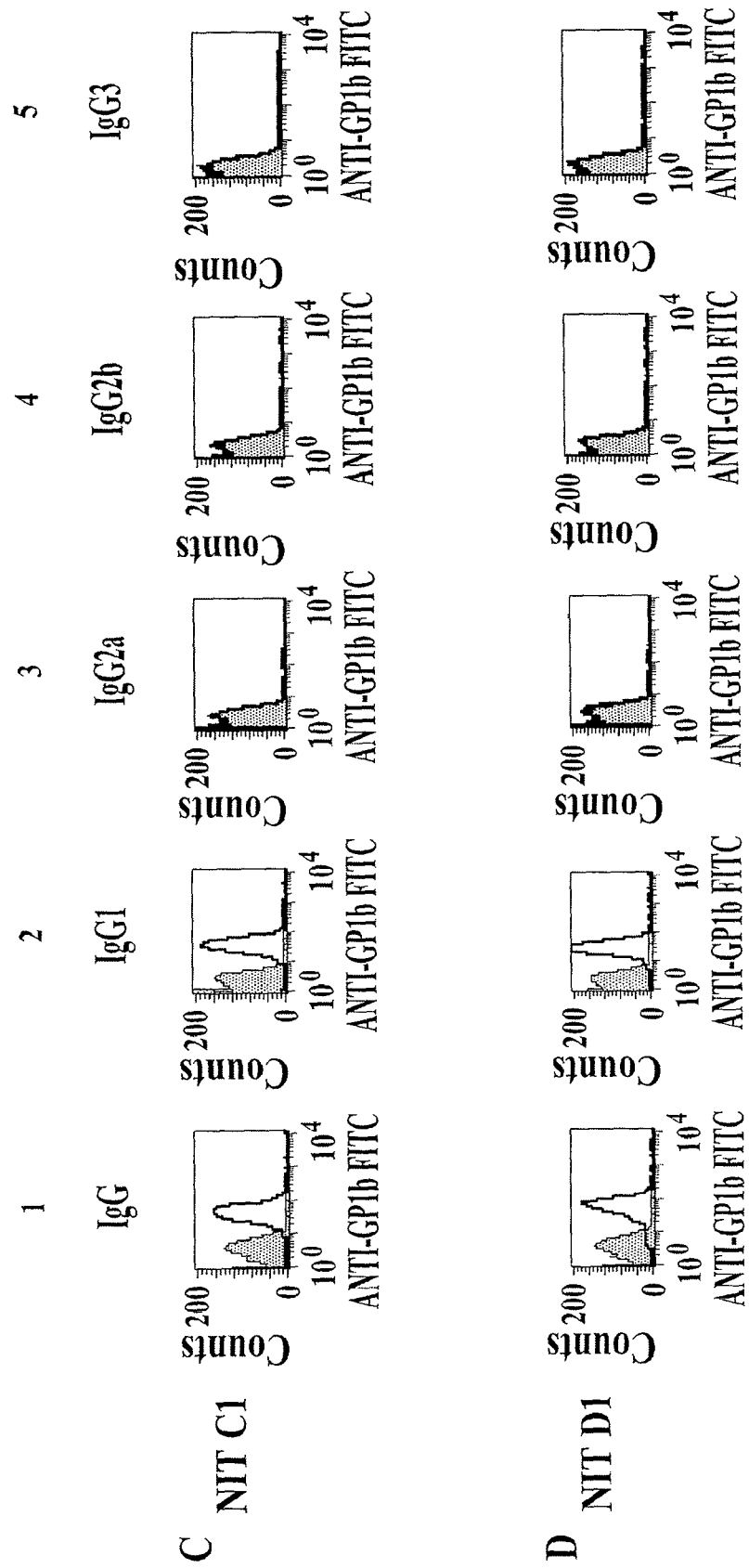
Figure 2B:
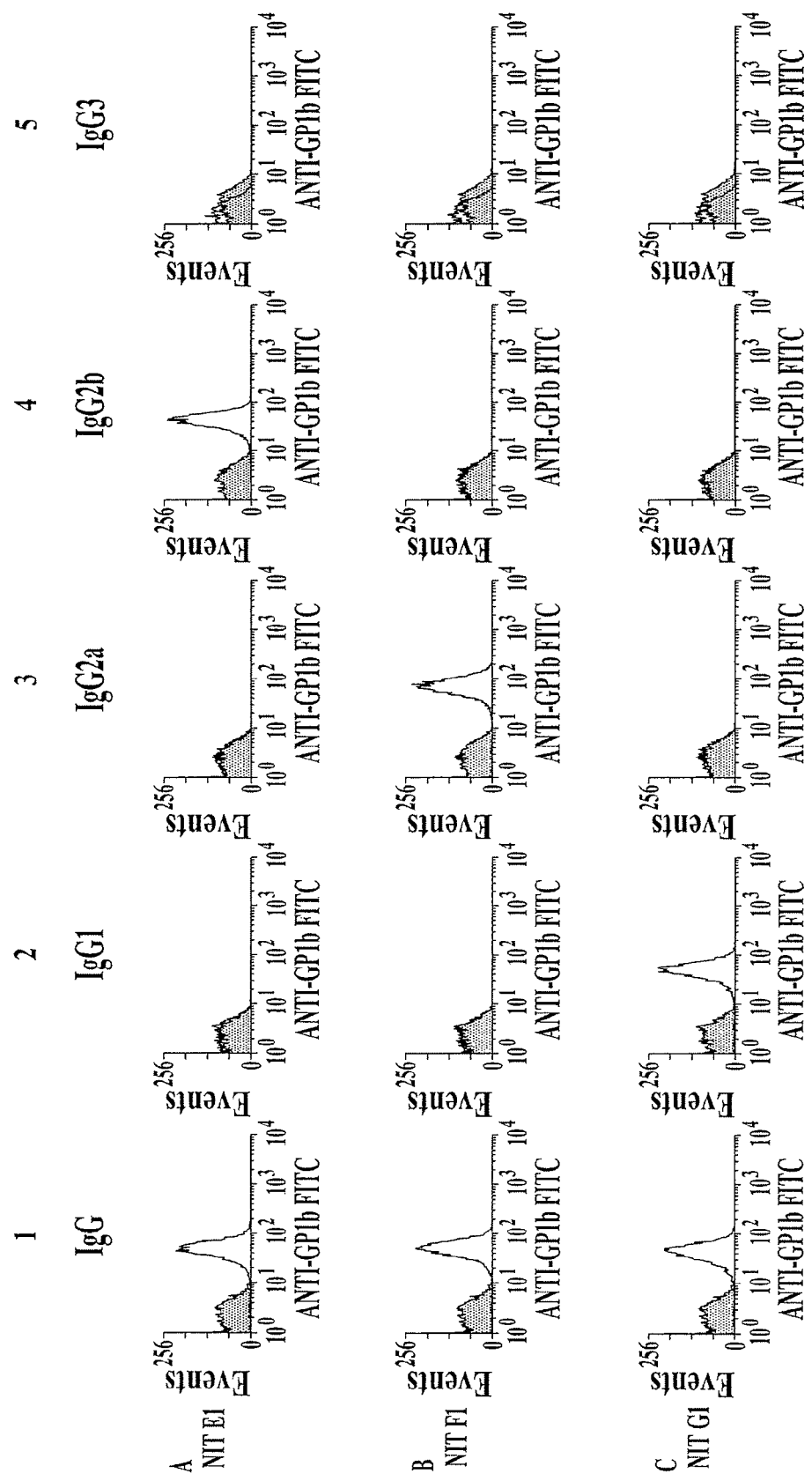
Figure 2B:
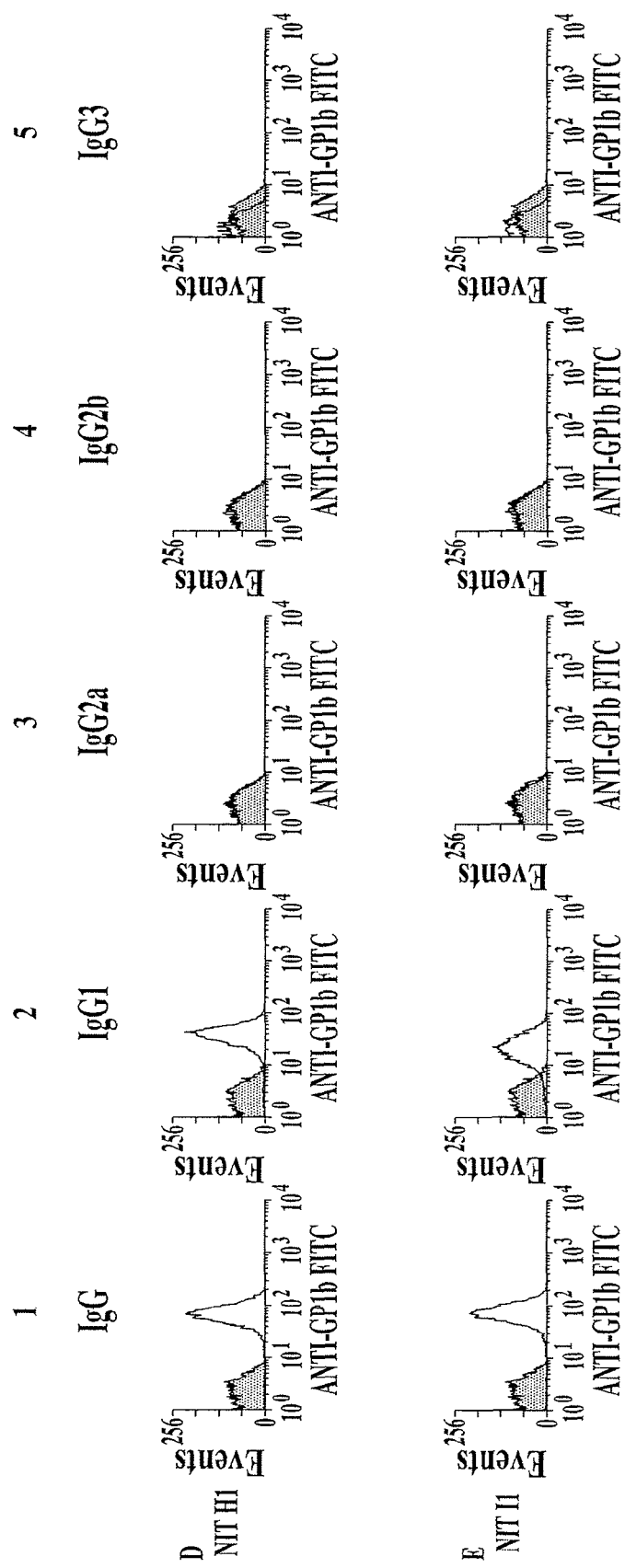

As indicated on FIGS. 2A and 2B, the NIT-A1, B1 and NIT-F1 clones are of the $IgG_{2a}$ subtype; the NIT-C1, NIT D1, NIT G1, H1 and I1 clones of the $IgG_1$ subtype and the NIT E1 clone of the $IgG_{2b}$ subtype.

EXAMPLE III

Bindings Characteristics of the Monoclonal Antibodies Specific for GPIbα

As shown in Example II, the monoclonal antibodies produced in Example I were shown to be capable of recognizing mouse platelets.

Figure 3:
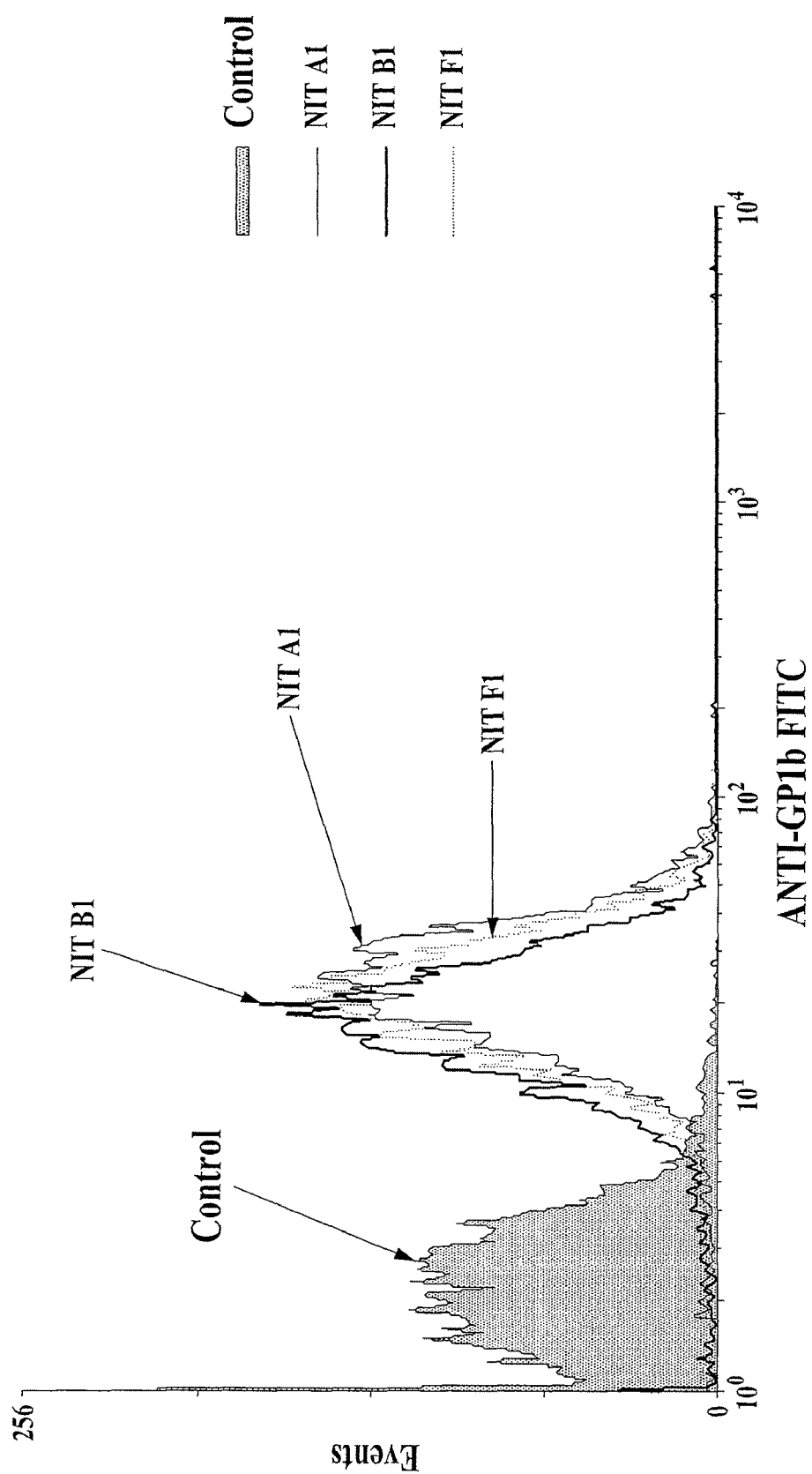
FIG. 3 is a graphical representation of flow cytometry results (counts in function of fluorescence) of human platelets incubated with (i) a control antibody, the NIT A1 clone, the NIT B1 clone or the NIT F1 clone and (ii) an anti-mouse IgG antibody labeled with FITC.

In order to assess if the monoclonal antibodies produced in Example I are also capable of recognizing human platelets, washed human platelets ($1 \times 10^6$) were incubated one hour with PBS (control), or a mAb produced according to the protocol set forth in Example I. The platelets were then incubated with FITC-labeled goat anti-mouse anti-GPIbα antibodies for 45 min. Samples were analyzed by flow cytometry. As shown on FIG. 3, NIT A1, NIT B1 and NIT F1 were shown to significantly bind to human platelets.

Figure 7:
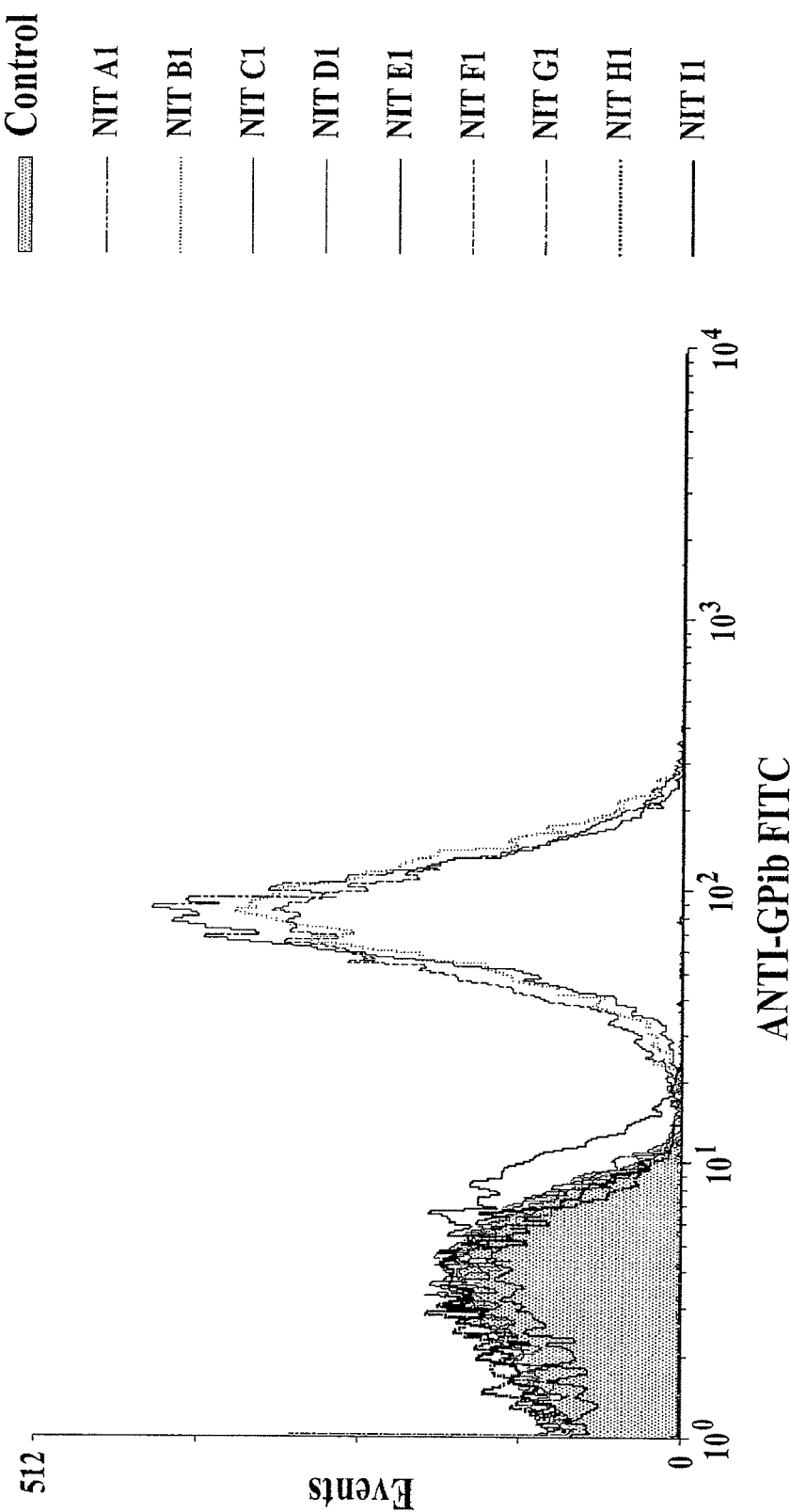
FIG. 7 shows a graphical representation of flow cytometry results (counts in function of fluorescence) of rat platelets incubated with (i) a control antibody, the NIT A1 clone, the NIT B1 clone, the NIT C1 clone, the NIT D1 clone, the NIT E1 clone, the NIT F1 clone, the NIT G1 clone, the NIT H1 clone or the NIT I1 clone and (ii) goat anti-mouse IgG antibody labeled with FITC.

In order to assess if the monoclonal antibodies produced in Example I are also capable of cross-reacting with rat platelets, washed rat platelets ($1\times10^6$) were incubated with PBS (control), or a mAb produced according to the protocol set forth in Example I. The platelets were then incubated with FITC-labeled goat anti-mouse IgG for 45 min and analyzed by flow cytometry. As shown in FIG. 7, NIT A1, B1 and F1 clone recognize rat platelets.

Figure 8:
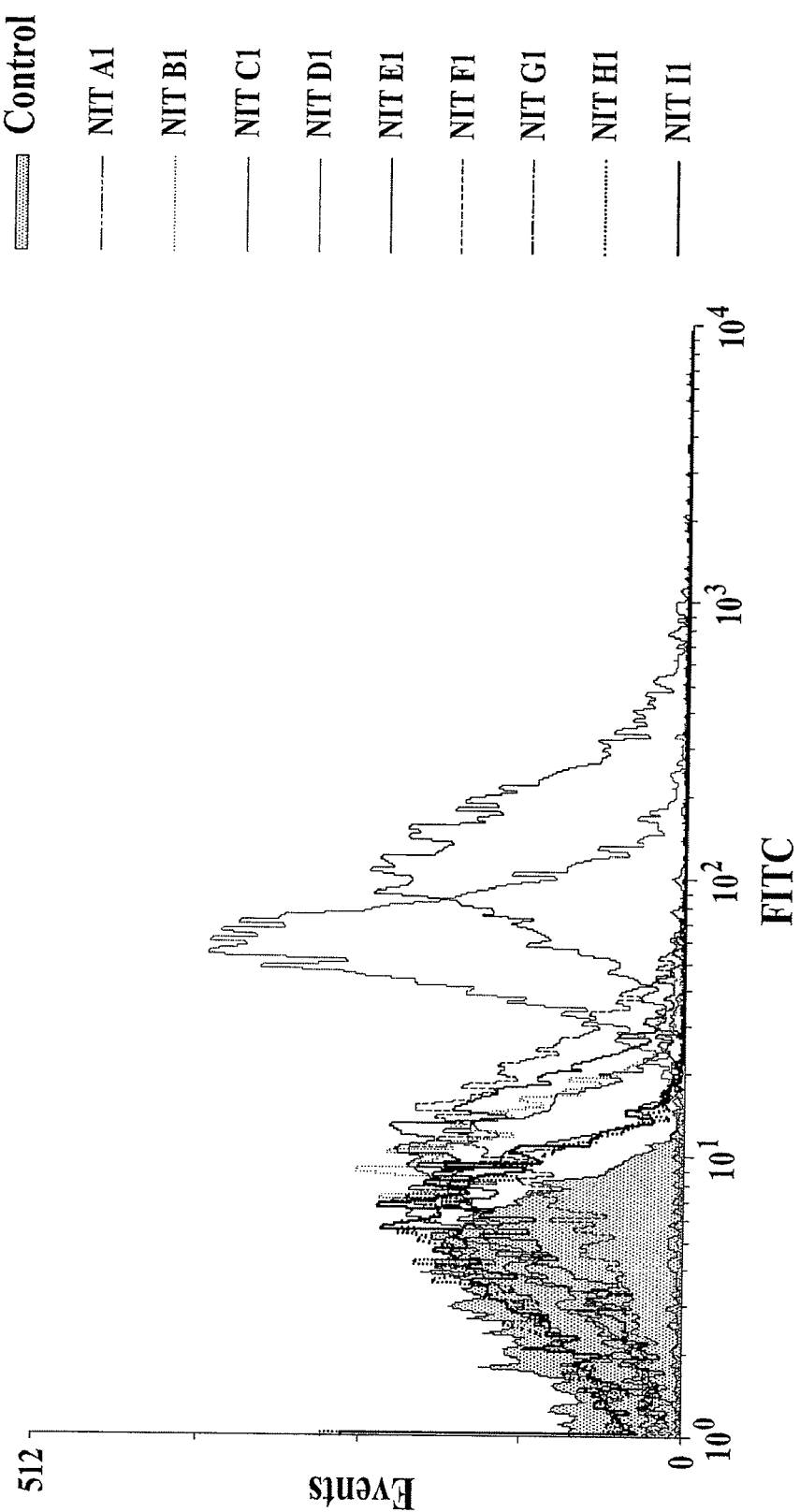
FIG. 8 shows a graphical representation of flow cytometry results (counts in function of fluorescence) of pig platelets incubated with (i) a control, the NIT A1 clone, the NIT B1 clone, the NIT C1 clone, the NIT D1 clone, the NIT E1 clone, the NIT F1 clone, the NIT G1 clone, the NIT H1 clone or the NIT I1 clone and (ii) goat anti-mouse IgG antibody labeled with FITC.

In order to assess if the monoclonal antibodies produced in Example I are also capable of cross-reacting with pig platelets, washed pig platelets ($1\times10^6$) were incubated with PBS (control), or a mAb produced according to the protocol set forth in Example I. The platelets were then incubated with FITC-labeled goat anti-mouse IgG for 45 min and analyzed by flow cytometry. As shown in FIG. 8, NIT C1 and D1 clones recognize pig platelets.

EXAMPLE III

Modulation of Platelet Aggregation by the Monoclonal Antibodies Specific for GPIbα

Figure 4:
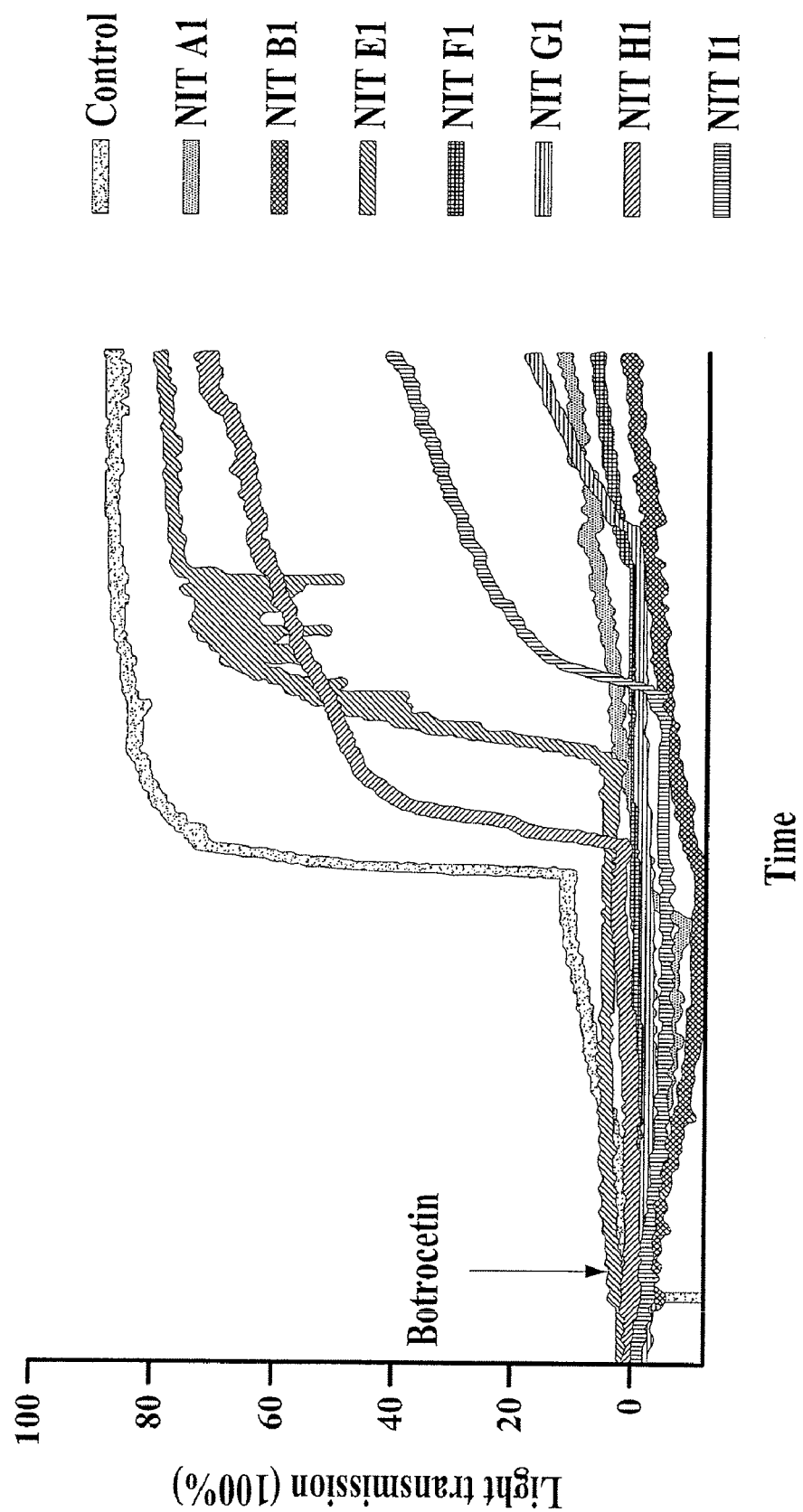
FIG. 4 is a graphical representation of standard aggregometry traces (% of light transmission in function of time (e.g., minutes)) of mouse platelets (i) first incubated with a control antibody, the NIT A1 clone, the NIT B1 clone, the NIT E1 clone, the NIT F1 clone, the NIT G1 clone, the NIT H1 clone and the NIT I1 clone and (ii) then aggregated with botrocetin (to induce platelet binding of the GPIbα receptor to the von Willebrand factor).

Mouse platelets (FIG. 4) were incubated with PBS (control), or 40 µg/mL of a mAb produced according to the protocol set forth in Example I (NIT A1, NIT B1, NIT E1, NIT F1, NIT G1, NIT H1 or NIT I1) then stimulated with botrocetin (20 µg/mL). Platelet aggregation (light transmission) was monitored over 16 min using a computerized Chrono-log aggregometer (Chrono-Log Corporation, Havertown, Pa., USA). As shown on FIG. 4, NIT A1, NIT B1, NIT F1, NIT G1, or NIT I1 significantly inhibited mouse platelet aggregation, NIT A1, NIT B1 and NIT F1 completely inhibited mouse platelet aggregation while NIT E1 and NIT H1 did not inhibit mouse platelet aggregation.

Figure 5:
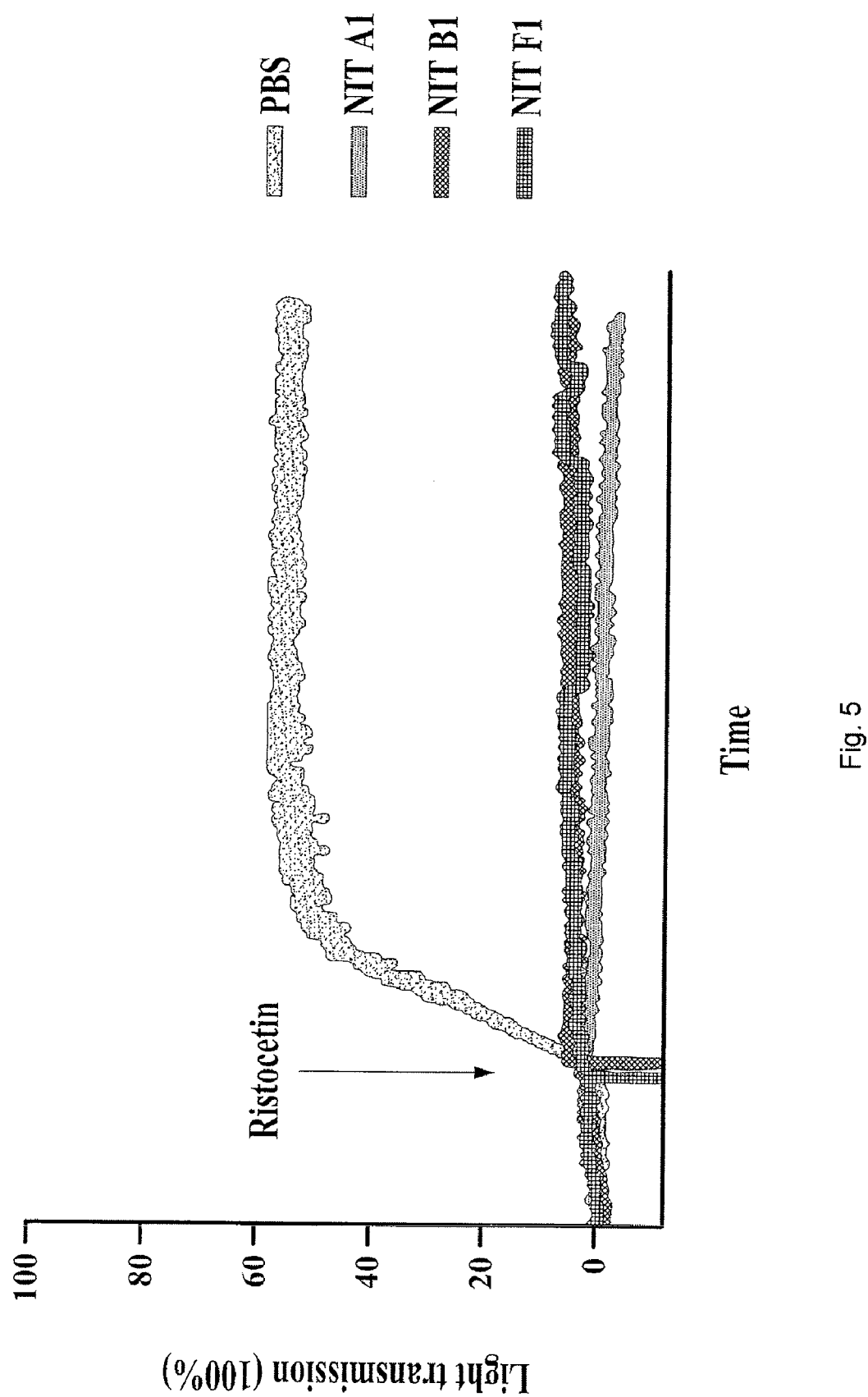
FIG. 5 is a graphical representation of standard aggregometry traces (% of light transmission in function of time (e.g., minutes)) of human platelets (i) first incubated with a control solution (e.g., PBS), the NIT A1 clone, the NIT B1 clone and the NIT F1 clone and (ii) then aggregated with ristocetin (to induce platelet binding of the GPIbα receptor to the von Willebrand factor).

Human platelets (FIG. 5) were incubated with PBS (control), or 40 µg/mL of a mAb produced according to the protocol set forth in Example I (NIT A1, NIT B1, NIT F1) then stimulated with ristocetin (1.5 µg/mL). Platelet aggregation (light transmission) was monitored over 16 min using a computerized Chrono-log aggregometer (Chrono-Log Corporation, Havertown, Pa., USA). As shown on FIG. 5, NIT A1, NIT B1 and NIT F1 significantly inhibited human platelet aggregation.

EXAMPLE IV

Modulation of Platelet Adhesion and Aggregation Ex Vivo by the Monoclonal Antibodies Specific for GPIbα

Figure 6:
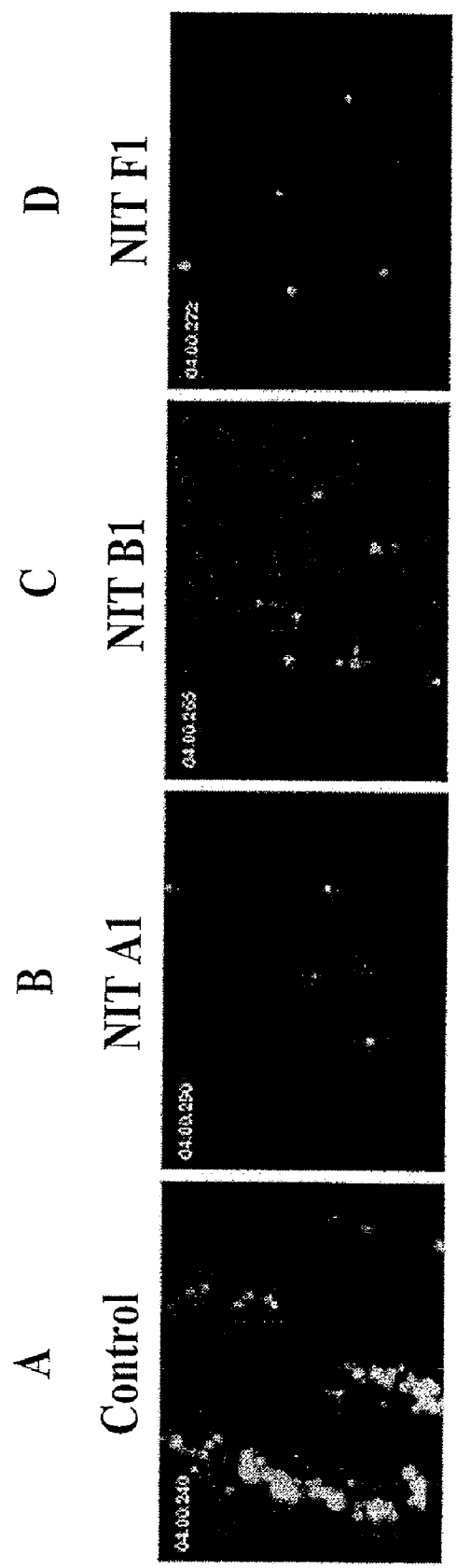
FIG. 6 shows fluorescence microscopy images of fluorescently labeled whole human blood pre-incubated with PBS (A) or and anti-GPIbα monoclonal antibody NIT A1 (B), NIT B1 (C) or NIT F1 (D) continuously perfused through collagen-coated microcapillary tubes at a wall shear rate of 1500/sec. Platelet adhesion and thrombus formation on collagen matrix was recorded in real-time over the course of the perfusion.

Fluorescently labeled heparin (40 IU/mL) anti-coagulated human whole blood was incubated with PBS (control; FIG. 6A) or with 10 mg/mL of a mAb produced by the protocol of Example I (NIT A1 (FIG. 6B), NIT B1 (FIG. 6C) or NIT F1 (FIG. 6D)) for 30 min. The blood was then perfused over a collagen coated surface at a shear rate of 1500 $s^{-1}$ (e.g., the arterial shear rate) for four minutes. Platelet adhesion and thrombus formation on the collagen coated surface was recorded in real time over the course of perfusion under a Zeiss Axiovert 135-inverted microscope (J Thromb Haemost. 2006 October; 4(10):2230-7; J Thromb Haemost. 2005 May; 3(5):875-83). As shown in FIG. 6, NIT A1, NIT B1 and NIT F1 almost completely inhibited human platelet adhesion and aggregation on the collagen coated surface.

Figure 9A:
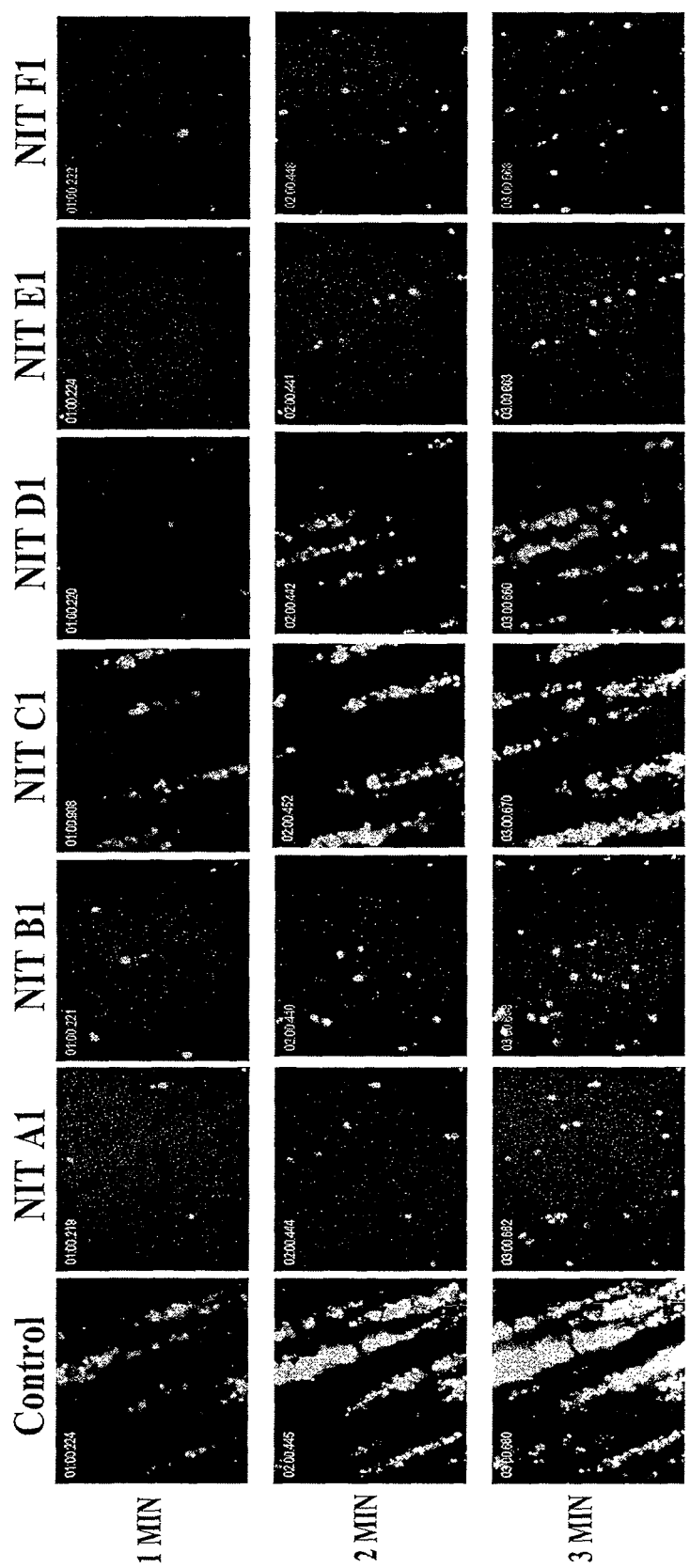
FIG. 9A shows fluorescence microscopy images of fluorescently labeled whole mouse blood pre-incubated with PBS (control) or and anti-GPIbα monoclonal antibody NIT A1, NIT B1, NIT C1, NIT D1, NIT E1 or NIT F1 continuously perfused through collagen-coated microcapillary tubes at a wall shear rate of 1200/sec. Platelet adhesion and thrombus formation on collagen matrix was recorded in real-time over the course of the perfusion.
Figure 9B:
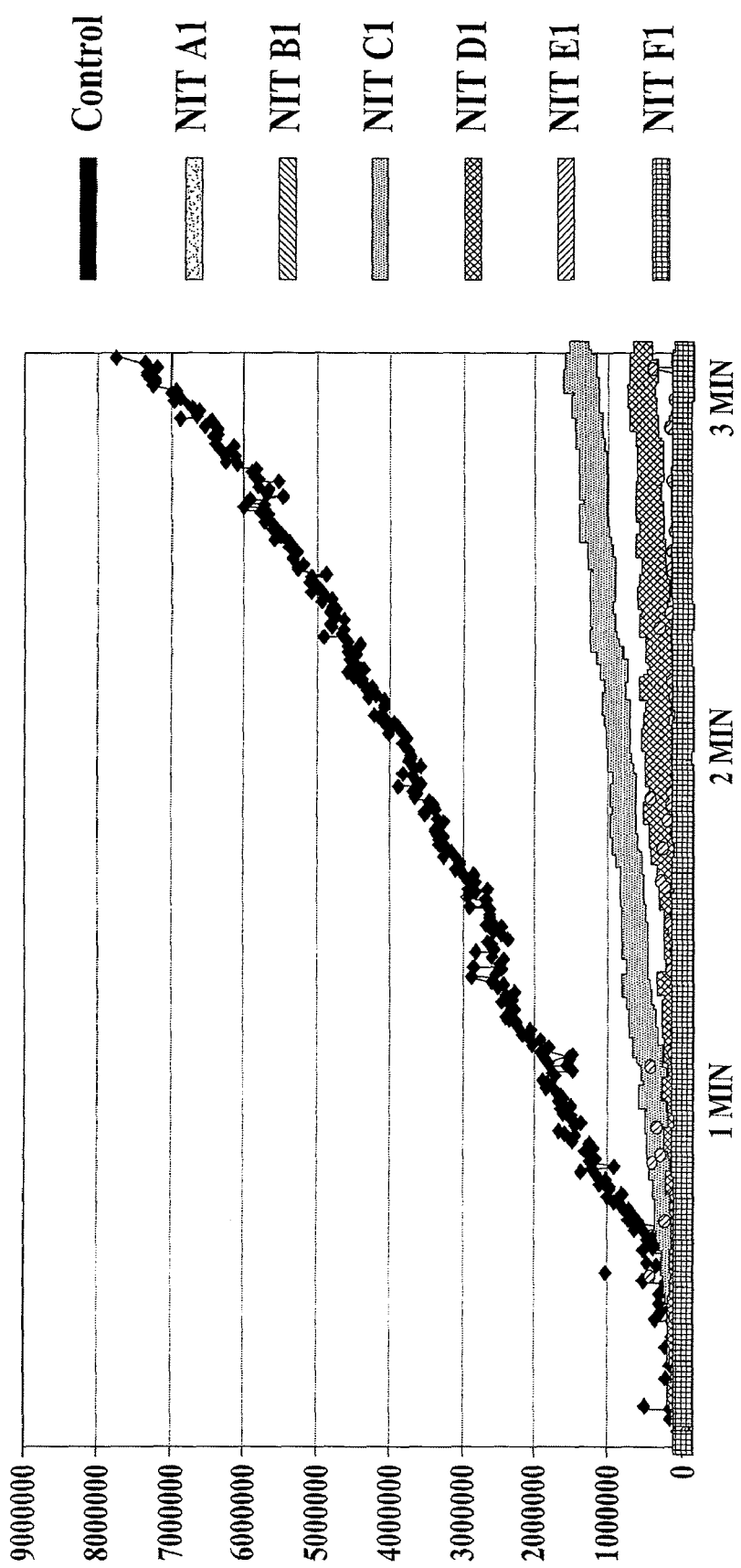
FIG. 9B shows a graphical representation of fluorescence intensity of platelet thrombi observed in FIG. 9A.

Fluorescently labeled heparin (40 IU/mL) anti-coagulated mouse whole blood was incubated with PBS (control; FIG. 9A) or with 10 mg/mL of a mAb produced by the protocol of Example I (NIT A1, NIT B1, NIT C1, NIT D1, NIT E1, NIT F1) for 30 min. The blood was then perfused over a collagen coated surface at a shear rate of 1200 $s^{-1}$ for three minutes. Platelet adhesion and thrombus formation on the collagen coated surface was recorded in real time over the course of perfusion under a Zeiss Axiovert 135-inverted microscope (J Thromb Haemost. 2006 October; 4(10):2230-7; J Thromb Haemost. 2005 May; 3(5):875-83; Reheman A. et al. Blood. 2009; February 19. 113: 1809-1817). As shown in FIG. 9A, NIT A1, NIT B1, NIT E1 and NIT F1 almost completely inhibited mouse platelet adhesion and aggregation on the collagen coated surface. The fluorescence intensity of platelet thrombi are shown in FIG. 9B.

EXAMPLE V

Modulation of Platelet Aggregation In Vivo by the Monoclonal Antibodies Specific for GPIbα

Platelets were fluorescently labeled and infused into 3- to 5-week-old anesthetized C57BL/6 WT mice. The mesentery was exposed through a midline abdominal incision. Vessel injury was generated by using a filter paper soaked with a $FeCl_3$ solution and placed over the vessel. The paper is then removed, and the vessel is covered with saline. Vessels were monitored for several minutes to 40 minutes after $FeCl_3$ treatment or until occlusion. To determine platelet tethering to injured vessels, $FeCl_3$ is superfused over mesenteric arterioles, and the number of fluorescently labeled platelets tethering to vessel walls is counted over a stretch of vessel as previously described (Ni H et al 2000 J Clin Invest. 106: 385-92; Yang H et al 2006 J Thromb Haemost. 4: 2230-7; Ni H et al 2003 Blood 102: 3609-14; Ni H et al 2003 Proc Natl Acad Sci USA 100: 2415-9). Time after $FeCl_3$ injury was either 5, 15 or 30 minutes. Blood flow was from right to left.

Figure 10:
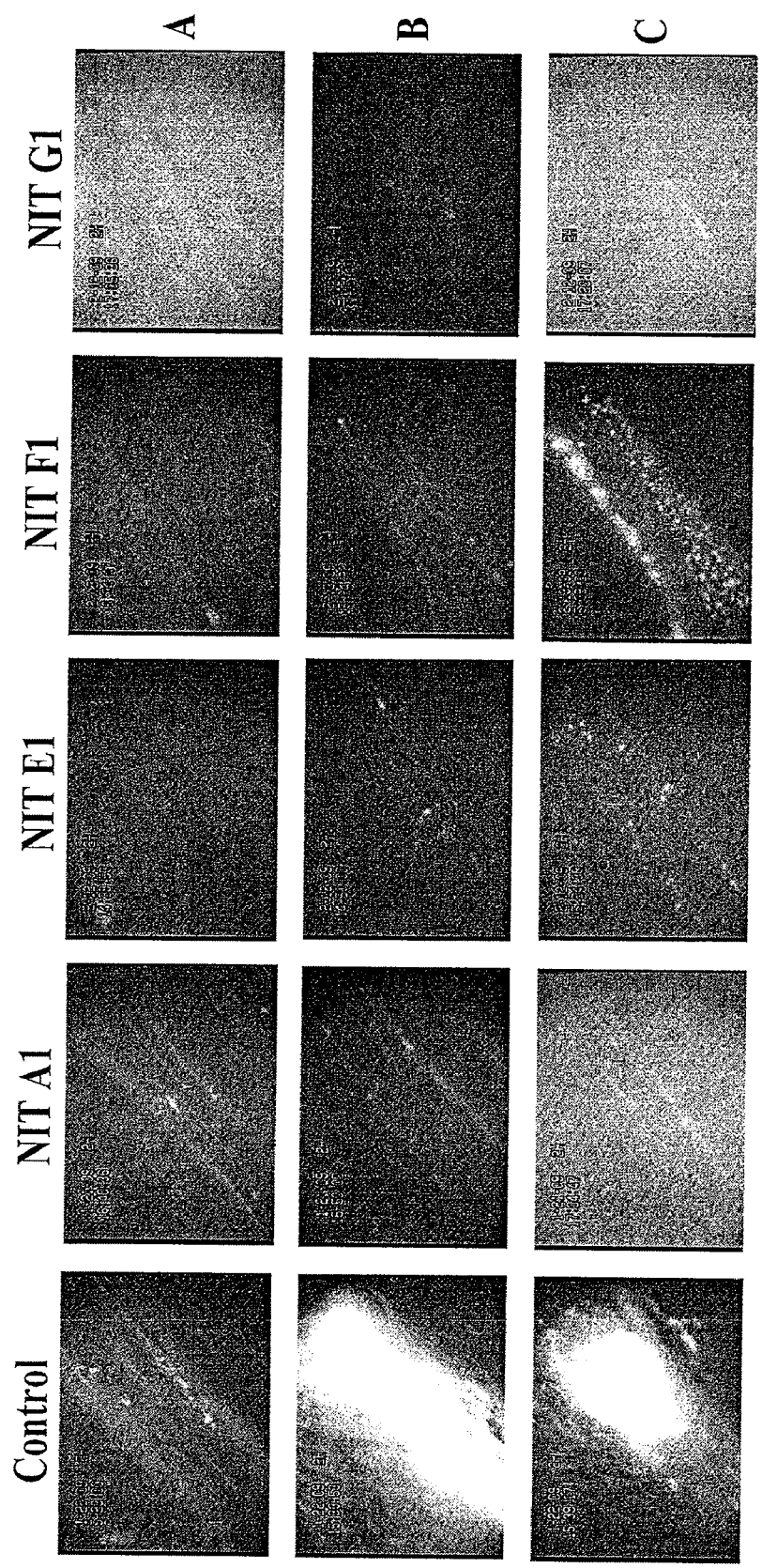
FIG. 10 shows intravital microscopy results for the in vivo thrombosis model in live mice. Time after $FeCl_3$ injury was either 5 min. (A), 15 min. (B) or 30 min. (C). The bright objects are fluorescently labeled platelets. A large thrombus at 15 minutes, and a vessel occlusion at 30 minutes were seen in control mice, but not in those mice treated with monoclonal antibodies against GPIbα (clone A1, E1, F1 and G1) after injury.

As shown on FIG. 10, in control mice, single fluorescent platelets start to adhere to the arterioles several minutes after injury and then, form visible thrombus which grew quickly to occluded injured arteriole. Compared to control mice, significant less platelets were adhered to the injured site of arteriole and thrombus formation was significantly inhibited in mice injected with anti-GPIbα mAbs described in Example I.

EXAMPLE VI

Induction of Thrombocytopenia

BALB/c mice platelets are enumerated on day 1 (basal count, 100%). Thrombocytopenia is induced by intravenously injection of one of three doses of anti-monoclonal antibodies 5 µg, 10 µg, 15 µg per mouse (n=6) of the antibodies produced by the protocol of Example I. Platelets are again enumerated 24 hours after antibody injection (day 2). Thrombocytopenia induction is represented in as the percent decrease in platelet count 24 hours after antibody injection. This method to induce thrombocytopenia has been already described in Blood 2006 108: 943-946.

Monoclonal antibodies capable of inducing thrombocytopenia in mice are considered as potential anti-thrombotic agents and research reagents for immune thrombocytopenia.

While the invention has been described in connection with specific embodiments thereof, it will be understood that it is capable of further modifications and this application is intended to cover any variations, uses, or adaptations of the invention following, in general, the principles of the present disclosure and including such departures from the present disclosure as come within known or customary practice within the art to which the invention pertains and as may be applied to the essential features hereinbefore set forth, and as follows in the scope of the appended claims.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An hybridoma cell line having an IDAC Accession No. selected from the group consisting of 071008-01 (NIT A1 clone), 071008-02 (NIT B1 clone), 071008-03 (NIT C1 clone), 071008-04 (NIT D1 clone), 071008-05 (NIT E1 clone), 071008-06 (NIT F1 clone), 071008-07 (NIT G1 clone), 071008-08 (NIT H1 clone) and 071008-09 (NIT I1 clone).

2. An isolated and purified antibody produced by the hybridoma cell line of claim 1.

3. An isolated and purified humanized antibody comprising an immunoglobulin variable region of a hybridoma antibody from an hybridoma cell line having an IDAC Accession No. selected from the group consisting of 071008-01 (NIT A1 clone), 071008-02 (NIT B1 clone), 071008-03 (NIT C1 clone), 071008-04 (NIT D1 clone), 071008-05 (NIT E1 clone), 071008-06 (NIT F1 clone), 071008-07 (NIT G1 clone), 071008-08 (NIT H1 clone) and 071008-09 (NIT I1 clone); and an immunoglobulin constant region from a human antibody.

4. The isolated and purified antibody of claim 2, wherein the isolated and purified antibody is labeled with a detectable marker or a conjugate.

5. A fragment of an isolated and purified antibody produced by the hybridoma cell line of claim 1, wherein the fragment is capable of specifically recognizing GPIbα.

6. A pharmaceutical composition or diagnosis composition comprising the isolated and purified antibody of claim 2 or the fragment of claim 5 that is capable of specifically recognizing GPIbα; and an acceptable carrier.

7. A solid phase having attached thereto the isolated and purified antibody of claim 2 or the fragment of claim 5 that is capable of specifically recognizing GPIbα.

8. The solid phase of claim 7, for the separation or isolation of a GPIbα receptor.

9. The solid phase of claim 7, for the separation or isolation of a platelet.

10. A method for reducing a likelihood of formation of a thrombus and/or the aggregation of platelets in an individual, said method comprising administering the isolated and purified antibody of claim 2 or claim 3, or the fragment of claim 5, in the individual, thereby reducing the likelihood of formation of the thrombus and/or the aggregation of platelets in the individual.

11. The method of claim 10, wherein the administration of the isolated and purified antibody or the fragment limits the size of the thrombus and/or the aggregate of platelets.

12. The method of claim 10, wherein the administration of the isolated and purified antibody or the fragment limits the number of thrombi and/or the aggregates of platelets in the individual.

13. A method of resolving thrombosis in an individual having a thrombus, said method comprising administering the isolated and purified antibody of claim 2 or the fragment of claim 5 in the individual, thereby resolving thrombosis in the individual.

14. The method of claim 13, wherein the administration of the isolated and purified antibody or the fragment limits the size of the thrombus.

15. The method of claim 13, wherein the administration of the isolated and purified antibody or the fragment limits the number of thrombi.

16. A method for determining the presence of a thrombus in an individual, said method comprising administering the isolated and purified antibody of claim 2 or claim 3, or the fragment of claim 5, to the individual, allowing the isolated and purified antibody or the fragment to form a complex with a GPIbα receptor on a platelet and determining the presence of the complex in said individual, wherein the isolated and purified antibody or the fragment is labeled with a detectable marker or a conjugate.

17. The method of claim 16, wherein the individual has received an antithrombotic agent prior to or after the administration of the isolated and purified antibody or the fragment.

18. The method of claim 16, wherein the isolated and purified antibody of claim 3 is administered, wherein the individual is a human and wherein the determination of the presence of the complex is repeated in time.

19. A method for determining platelet count in a sample from an individual, said method comprising contacting the isolated and purified antibody of claim 2 or claim 3, or the fragment of claim 5, with the sample from the individual to form a complex between (i) the isolated and purified antibody of the fragment and (ii) the platelet and detecting the presence of the complex to determine the platelet count in the sample.

20. A method for tracking a platelet in an individual, said method comprising administering the isolated and purified antibody of claim 2 or claim 3, or the fragment of claim 5, to the individual, allowing for a complex between (i) the isolated and purified antibody or the fragment and (ii) the platelet to be formed, detecting the complex and its location to track the platelet, wherein the isolated and purified antibody or the fragment is labeled with a detectable marker or a conjugate.

21. The method of claim 20, wherein the isolated and purified antibody of claim 3 is administered, wherein the individual is a human and wherein the detection is repeated in time.

* * * * *